United States Patent
Fujii et al.

(10) Patent No.: US 8,186,384 B2
(45) Date of Patent: May 29, 2012

(54) FLOW CONTROL APPARATUS AND MEDICAL INJECTION CIRCUIT USING THE SAME

(75) Inventors: Ryoji Fujii, Hiroshima (JP); Takehiko Yuki, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 988 days.

(21) Appl. No.: 12/087,726

(22) PCT Filed: Jan. 15, 2007

(86) PCT No.: PCT/JP2007/050424
§ 371 (c)(1),
(2), (4) Date: Jul. 14, 2008

(87) PCT Pub. No.: WO2007/083599
PCT Pub. Date: Jul. 26, 2007

(65) Prior Publication Data
US 2009/0018513 A1    Jan. 15, 2009

(30) Foreign Application Priority Data
Jan. 17, 2006  (JP) .................................. 2006-009123

(51) Int. Cl.
*F16K 15/14*   (2006.01)
(52) U.S. Cl. ..................... 137/854; 251/342; 604/247
(58) Field of Classification Search ........... 137/513.7, 137/516.11, 601.2, 854; 251/342; 604/247, 604/250
See application file for complete search history.

(56) References Cited

U.S. PATENT DOCUMENTS

| | | | | |
|---|---|---|---|---|
| 4,642,097 A | * | 2/1987 | Siposs | 604/119 |
| 4,725,266 A | * | 2/1988 | Siposs | 604/119 |
| 2001/0021829 A1 | | 9/2001 | Hiejima | |
| 2002/0002350 A1 | | 1/2002 | Larrain et al. | |
| 2005/0028404 A1 | * | 2/2005 | Marvin et al. | 36/45 |
| 2006/0155248 A1 | | 7/2006 | Hashimoto et al. | |

FOREIGN PATENT DOCUMENTS

| | | |
|---|---|---|
| GB | 1 300 348 | 12/1972 |
| JP | 46-003794 A | 11/1971 |
| JP | 51-042772 | 11/1976 |
| JP | 61-124640 | 8/1986 |
| JP | 2001-238950 A | 9/2001 |

(Continued)

*Primary Examiner* — Kevin Lee
*Assistant Examiner* — Macade Brown
(74) *Attorney, Agent, or Firm* — Hamre, Schumann, Mueller & Larson, P.C.

(57) ABSTRACT

A flow control apparatus 1 including a tubular outside member 4, a tubular inside member 10 placed in the outside member 4, and a valve member 20 is used. The inside member 10 includes a through-hole 14 passing through a side wall in a thickness direction and a contact portion 11 that is in contact with the outside member 4, which are arranged in that order in a direction from one opening 16 to the other opening 17. The valve member 20 is placed in the opening 17 of the inside member 10. The valve member 20 passes only a fluid supplied at a set pressure or higher in a direction from the one opening 16 to the other opening 17. The outside member 4 is formed so as to form a gap communicating with the through hole 14 between the outside member 4 and the contact portion 11 due to elastic deformation caused by an external force. The gap forms a flow path of a fluid in combination with the through-hole 14.

8 Claims, 15 Drawing Sheets

FOREIGN PATENT DOCUMENTS

| | | |
|---|---|---|
| JP | 2002-095744 A | 4/2002 |
| JP | 2004-501686 A | 1/2004 |
| JP | 2004-073822 A | 3/2004 |
| JP | 2005-016610 A | 1/2005 |
| WO | WO 2004/016314 A1 | 2/2004 |
| WO | WO 2004/052428 A1 | 6/2004 |

* cited by examiner

FLOW CONTROL APPARATUS AND MEDICAL INJECTION CIRCUIT USING THE SAME

TECHNICAL FIELD

The present invention relates to a flow control apparatus, and in particular, to a flow control apparatus that functions as an anti-free flow mechanism during the injection of a transfusion and the administration of a drug with respect to a patient, and an injection circuit using the flow control apparatus.

BACKGROUND ART

Conventionally, in order to define the flow rate of a transfusion to be injected into a patient, a transfusion pump has been used. The transfusion pump is attached to a transfusion circuit connecting a transfusion bag to a puncture needle and provides a transfusion tube constituting the transfusion circuit with a peristalsis, thereby feeding a transfusion at a set flow rate. Furthermore, generally, as the transfusion pump, a finger-type transfusion pump and a roller-type transfusion pump are known.

The finger-type transfusion pump includes a plurality of fingers arranged in a row along a transfusion tube, and allows the plurality of fingers to reciprocate separately, thereby providing the transfusion tube with a peristalsis. Furthermore, the roller-type transfusion pump includes a pair of rotation rollers and allows them to perform a circulation motion, thereby providing the transfusion pump with a peristalsis.

The injection of a transfusion using such transfusion pumps has a free-flow problem. The free-flow refers to the following: when a transfusion pump is removed while a clamp provided in the vicinity of a puncture needle of a transfusion tube is not closed after the process of transfusing is completed, a transfusion in an amount more than necessary is injected into a patient's body.

Furthermore, the free-flow problem may occur even in the case of the administration of a drug through a syringe pump. For example, in the case where a syringe is removed from a pump body when a patient pulls a drug tube or the like, a drug in an amount more than a defined amount may be injected into a patient. Furthermore, if a drug in an amount more than necessary is administered in the administration of a drug, the life of a patient may be threatened. Thus, to prevent free-flow is more important in the administration of a drug than in the process of transfusing.

In order to solve such a free-flow problem, for example, a transfusion pump equipped with an anti-free flow mechanism has been proposed for example, see Patent Document 1). The anti-free flow mechanism disclosed in Patent Document 1 is composed of an open/close device for opening/closing a dedicated clip previously attached to a transfusion tube. The open/close apparatus is contained in a transfusion pump body, and when a user opens an open/close door of a transfusion pump so as to remove the transfusion tube, the above-mentioned dedicated clip is closed automatically to crush the transfusion tube, thereby stopping the injection of a transfusion.

Accordingly, if the transfusion pump disclosed in Patent Document 1 is used, even if an attempt is made so as to remove the transfusion tube from the transfusion pump while a clamp is open, the injection of a transfusion into a patient in an amount more than necessary is suppressed by the anti-free flow mechanism.

In addition, as a method for preventing free-flow, it is conceivable to use a method for incorporating a valve apparatus that does not pass a fluid unless a pressure reaches a set value or higher in an injection circuit (for example, see Patent Document 2). In the injection circuit in which the valve apparatus is incorporated, it is considered that a fluid does not flow at a low pressure (head pressure) at a time free-flow occurs, so that free-flow can be prevented.
Patent Document 1: JP 2004-73822 A
Patent Document 2: JP 2004-501686 A

DISCLOSURE OF INVENTION

Problem to be Solved by the Invention

However, the above-mentioned anti-free flow mechanism disclosed in Patent Document 1 has the following problem: the anti-free flow mechanism is contained in a transfusion pump, so that it cannot be applied to another existing transfusion pump. There also is the following problem: a transfusion tube with a dedicated clip attached thereto previously is required for using the above-mentioned anti-free flow mechanism disclosed in Patent Document 1, so that an existing transfusion tube cannot be used.

Thus, in order to use the above-mentioned anti-free flow mechanism disclosed in Patent Document 1, it is necessary to newly purchase a transfusion pump and a transfusion tube, which may increase a treatment cost. There also is a problem that a syringe pump cannot be applied to the above-mentioned anti-free flow mechanism disclosed in Patent Document 1 in terms of a structure.

On the other hand, the above-mentioned valve apparatus disclosed in Patent Document 2 can be applied to existing various pumps, which can minimize the increase in a treatment cost. However, when the above-mentioned valve apparatus disclosed in Patent Document 2 is incorporated in an injection circuit, it becomes impossible to perform priming, using a head pressure. This makes it necessary to attach a valve apparatus after the completion of priming, resulting in a complicated priming operation.

An object of the present invention is to provide a flow control apparatus that solves the above-mentioned problems, is applicable irrespective of the kind and structure of a pump, and is capable of suppressing the occurrence of free-flow without making a priming operation complicated, and an injection circuit using the flow control apparatus.

Means for Solving Problem

In order to achieve the above object, a flow control apparatus of the present invention includes: a tubular outside member; a tubular inside member inserted in the outside member; and a valve member, wherein the inside member includes a through-hole passing through a side wall of the inside member in a thickness direction and a contact portion that is in contact with the outside member in an order in a direction from one opening of the inside member to the other opening thereof, the valve member is placed in the other opening of the inside member, and passes only a fluid supplied at a set pressure or higher from the one opening of the inside member to the other opening thereof, the outside member is formed so as to be deformed elastically, thereby forming a gap communicating with the through-hole between the outside member and the contact portion, and the gap forms a flow path of a fluid together with the through-hole.

Furthermore, in order to achieve the above object, an injection circuit of the present invention includes at least the above-mentioned flow control apparatus of the present invention, a first tube, and a second tube, wherein the first tube is connected to the one opening of the inside member of the flow control apparatus, and the second tube is connected to the other opening of the outside member of the flow control apparatus.

Effects of the Invention

Based on the above configuration, according to the flow control apparatus and the injection circuit of present invention, for example, the set pressure of a valve member can be set to be a value higher than that of a flow pressure at a time of the occurrence of free-flow, whereby the occurrence of free-flow can be suppressed. Furthermore, in the flow control apparatus and the injection circuit in the present invention, an outside member can be deformed elastically, whereby another flow path that does not pass through a valve member can be formed. Thus, the use of another flow path enables priming by a head pressure and avoids complications for a priming operation. Furthermore, the flow control apparatus of the present invention can be incorporated in an injection circuit easily, and is applicable irrespective of the kind and structure of a pump.

BRIEF DESCRIPTION OF DRAWINGS

FIG. 1 shows views illustrating an outer appearance of a flow control apparatus in Embodiment 1 of the present invention.

FIG. 2 shows cross-sectional views illustrating a configuration of the flow control apparatus shown in FIG. 1.

FIG. 4 shows views illustrating an inside member constituting the flow control apparatus shown in FIG. 1.

FIG. 5 shows views illustrating a valve member constituting the flow control apparatus shown in FIG. 1.

FIG. 12 shows views illustrating an inside member constituting the flow control apparatus shown in FIG. 11.

FIG. 13 shows views illustrating an outer appearance of a flow control apparatus in Embodiment 3 of the present invention.

FIG. 14 shows cross-sectional views illustrating a configuration of the flow control apparatus shown in FIG. 13.

FIG. 16 shows cross-sectional views taken along a cut line I-I' in FIG. 15A.

DESCRIPTION OF THE INVENTION

Figure 1A:
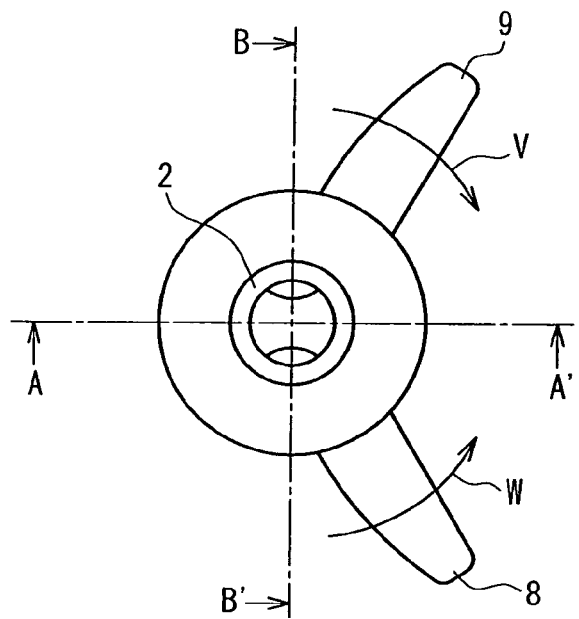
FIG. 1A is a top view.

A flow control apparatus of the present invention includes: a tubular outside member; a tubular inside member inserted in the outside member; and a valve member, wherein the inside member includes a through-hole passing through a side wall of the inside member in a thickness direction and a contact portion that is in contact with the outside member in an order in a direction from one opening of the inside member to the other opening thereof. The valve member is placed in the other opening of the inside member, and passes only a fluid supplied at a set pressure or higher from the one opening of the inside member to the other opening thereof. The outside member is formed so as to be deformed elastically, thereby forming a gap communicating with the through-hole between the outside member and the contact portion, and the gap forms a flow path of a fluid together with the through-hole.

In the above-mentioned flow control apparatus of the present invention, it is preferred that a convex portion is formed along an outer periphery of the inside member, and a top portion of the convex portion forms the contact portion. In this case, a gap to be a flow path can be formed easily when the outside member is deformed elastically.

Furthermore, in the above-mentioned flow control apparatus of the present invention, it is preferred that the inside member further includes a second contact portion that is in contact with the outside member in a portion positioned on one side of the through-hole, and the outside member is formed so as to cause elastic deformation in a region other than the portion that is in contact with the second contact portion, which is larger than that in the portion that is in contact with the second contact portion. According to the above embodiment, since the inside member is in contact with the outside member via the second contact portion even if the outside member is deformed elastically, a fluid is unlikely to leak outside of the flow control apparatus.

In the above-mentioned embodiment, it is preferred that a groove is formed along an outer periphery of the outside member between the portion that is in contact with the second contact portion of the outside member and the region other than the portion that is in contact with the second contact portion on an outer surface of the outside member. This further can strengthen the contact between the second contact portion of the inside member and the outside member when the outside member is deformed elastically.

Furthermore, in the above-mentioned embodiment, it also is preferred that the outside member includes a thin portion whose thickness is smaller than that in the portion that is in contact with the second contact portion in the region other than the portion that is in contact with the second contact portion. This also can strengthen the contact between the second contact portion of the inside member and the outside member when the outside member is deformed elastically.

Furthermore, in the above-mentioned embodiment, it is preferred that a member protruding from an outer surface of the outside member is provided in the region other than the portion that is in contact with the second contact portion of the outside member. In this case, a user of the flow control apparatus can elastically deform the outside member easily using the protruding member.

Furthermore, it also is preferred that a portion on the other side of the outside member has a small diameter, a pair of members protruding toward the other side are provided on the portion on the other side of the portion that is in contact with the contact portion in the outside member, and the pair of members are placed so that one member and the other member are opposed to each other with the small-diameter portion interposed therebetween. Even in this case, a user of the flow control apparatus can elastically deform the outside member easily using the pair of protruding members.

Furthermore, in the above-mentioned flow control apparatus of the present invention, it is preferred to use a valve member including a valve portion in an umbrella shape formed so as to cover and close the other opening of the inside member, and a protruding portion that protrudes from the valve portion and is inserted in the inside member from the other opening of the inside member, wherein the protruding portion is formed so that a gap to be a flow path of a fluid is present between the protruding portion and an inner surface of the inside member when the protruding portion is inserted in the inside member, is fixed to the inside member while the other opening of the inside member is closed with the valve portion, and further is deformed elastically to cancel closing by the valve portion when the valve portion is pressed with a fluid supplied through the gap between the inner surface of the inside member and the protruding portion at the set pressure or higher. In this case, the precision of the set pressure can be enhanced, and the exactness of an operation in the case where a fluid is supplied at the set pressure can be enhanced.

Furthermore, an injection circuit of the present invention includes at least the above-mentioned flow control apparatus of the present invention, a first tube, and a second tube, wherein the first tube is connected to the one opening of the inside member of the flow control apparatus, and the second tube is connected to the other opening of the outside member of the flow control apparatus.

Embodiment 1

Hereinafter, the flow control apparatus and the injection circuit in Embodiment 1 of the present invention will be described with reference to FIGS. 1 to 10. First, the flow control apparatus in Embodiment 1 will be described using FIGS. 1 to 7.

Figure 1B:
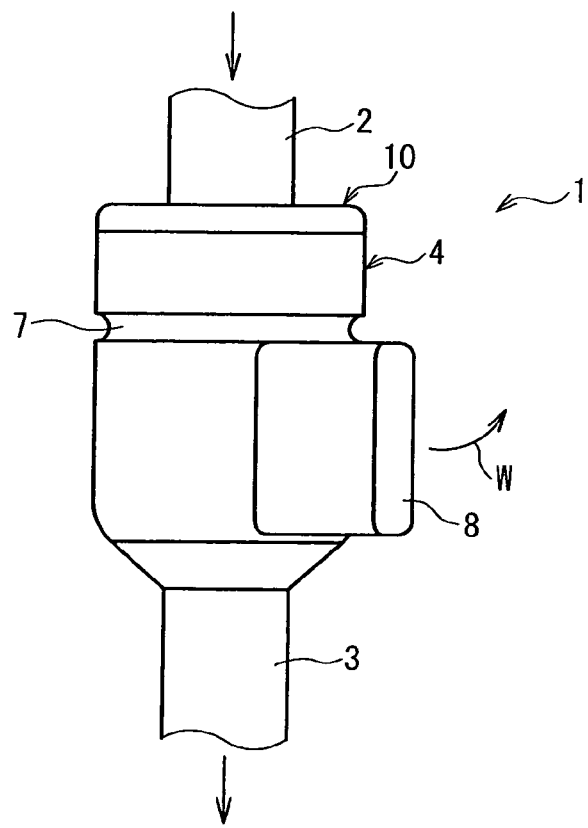
FIG. 1B is a side view.
Figure 2A:
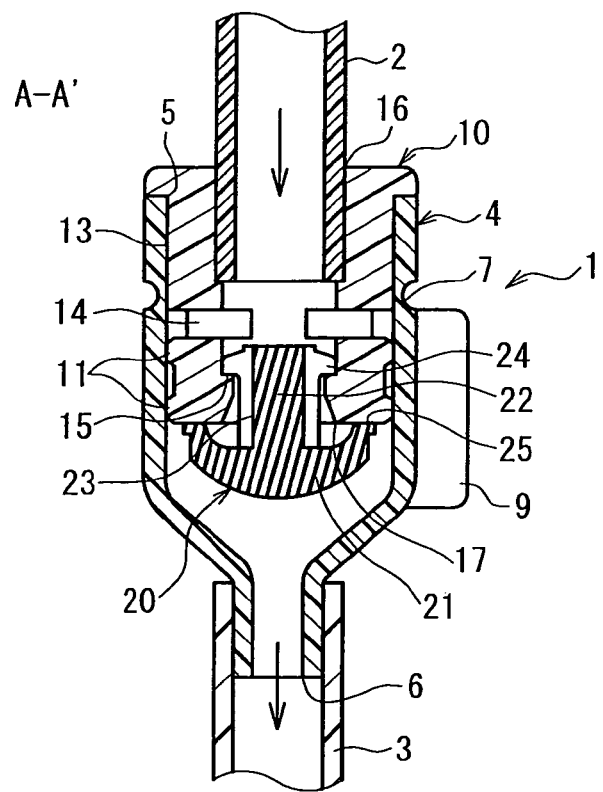
FIG. 2A is a cross-sectional view taken along a cut line A-A in FIG. 1A.
Figure 2B:
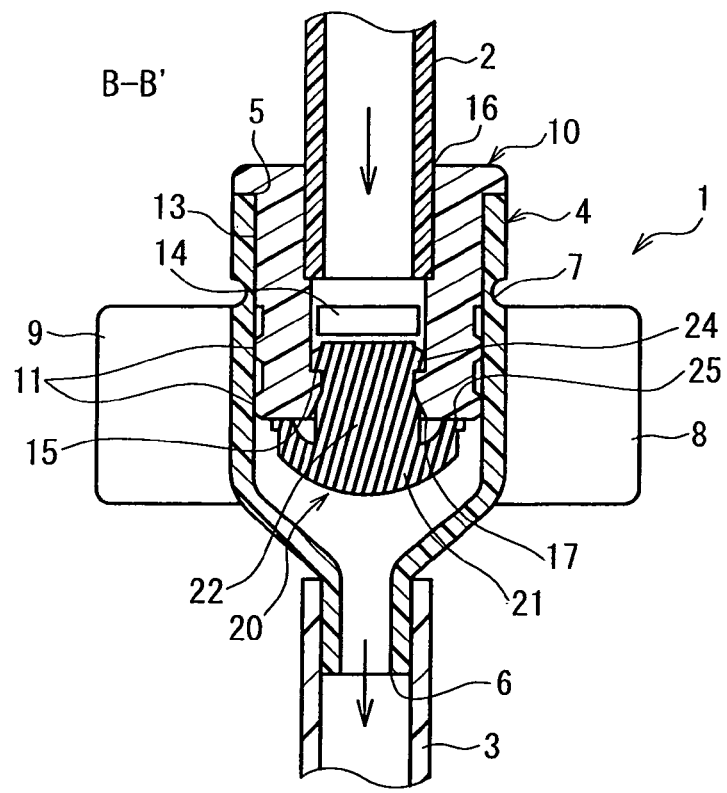
FIG. 2B is a cross-sectional view taken along a cut line B-B' in FIG. 1B.

FIG. 1 shows views illustrating an outer appearance of a flow control apparatus in Embodiment 1 of the present invention, FIG. 1A is a top view, and FIG. 1B is a side view. FIG. 2 shows cross-sectional views illustrating a configuration of the flow control apparatus shown in FIG. 1, FIG. 2A is a cross-sectional view taken along a cut line A-A' in FIG. 1A, and FIG. 2B is a cross-sectional view taken along a cut line B-B' in FIG. 1B. In FIGS. 1 and 2, arrows (excluding arrows V and W) represent flow directions of a fluid.

Figure 3:
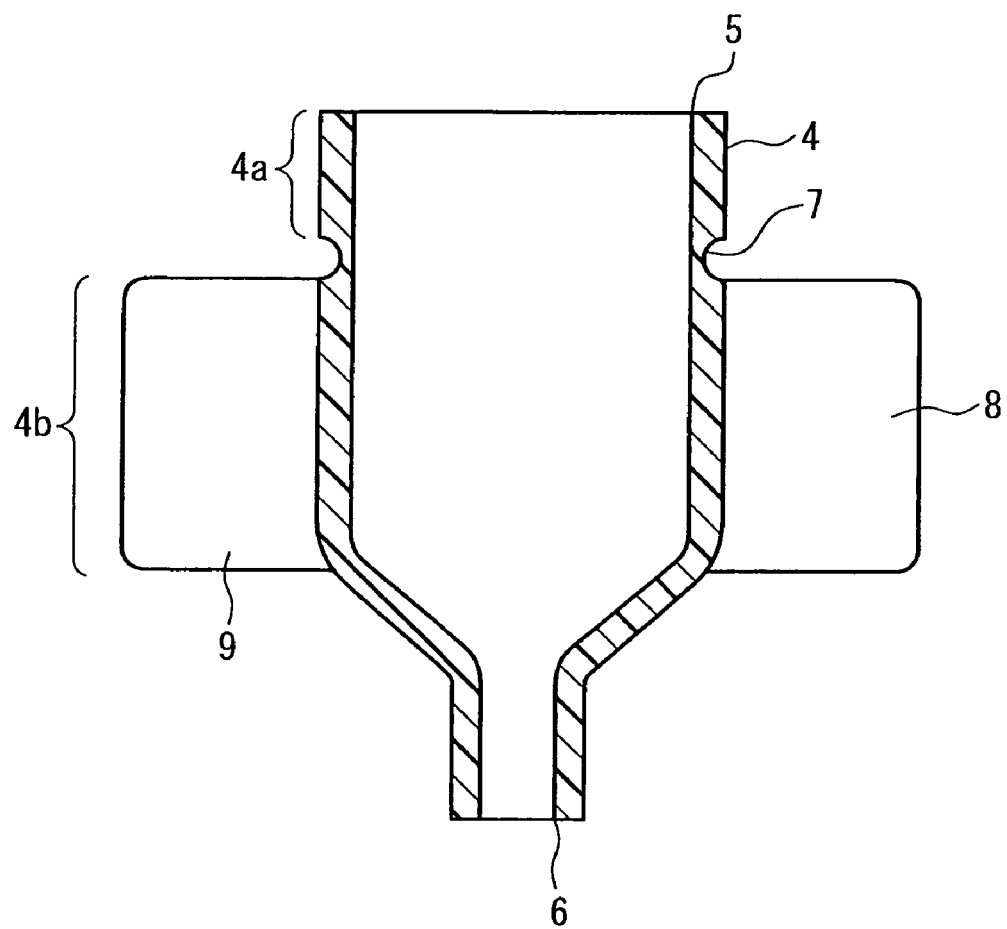
FIG. 3 is a cross-sectional view showing a outside member constituting the flow control apparatus shown in FIG. 1.

FIG. 3 is a cross-sectional view showing an outside member constituting the flow control apparatus shown in FIG. 1.

Figure 4A:
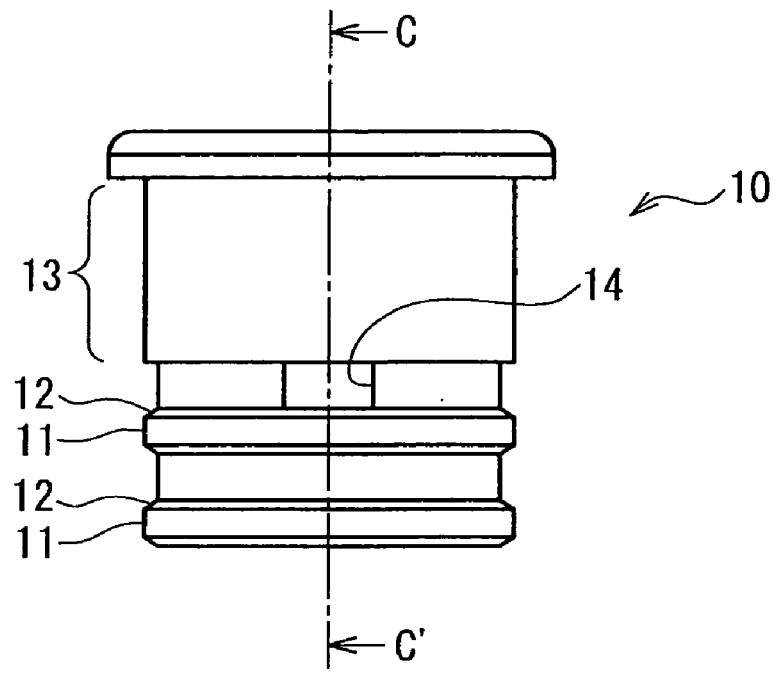
FIG. 4A is a side view.
Figure 4B:
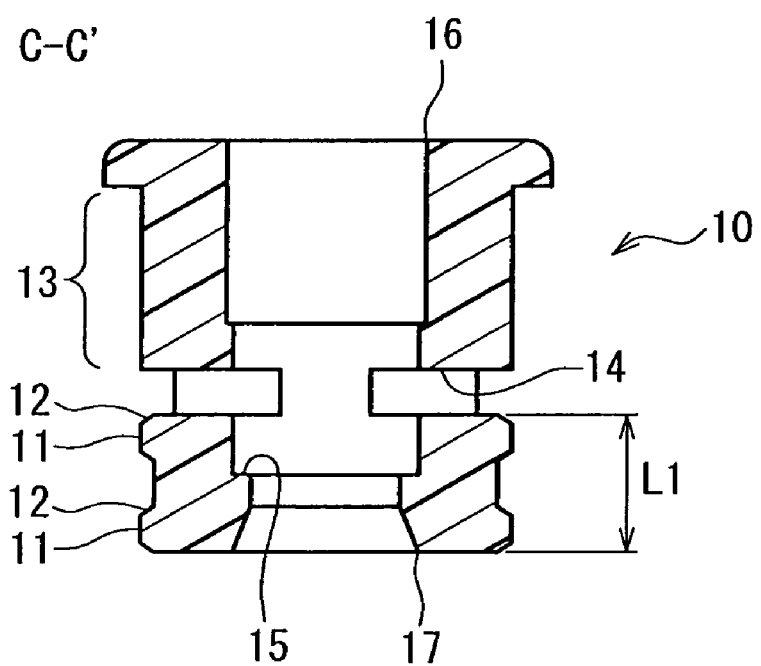
FIG. 4B is a cross-sectional view taken along a cut line C-C' in FIG. 4A.

FIG. 4 shows views illustrating an inside member constituting the flow control apparatus shown in FIG. 1, FIG. 4A is a side view, and FIG. 4B is a cross-sectional view taken along a cut line C-C' in FIG. 4A.

Figure 5A:
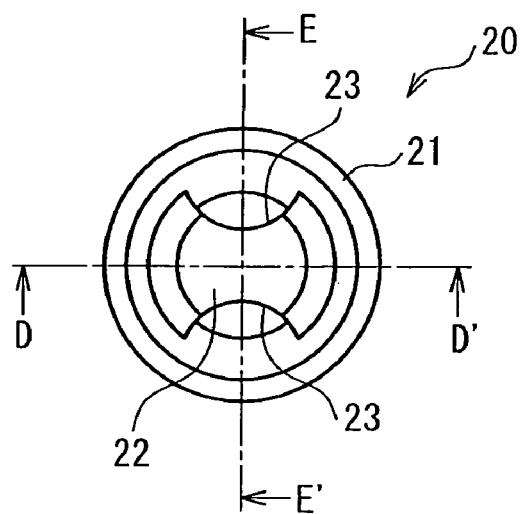
FIG. 5A is a top view.
Figure 5B:
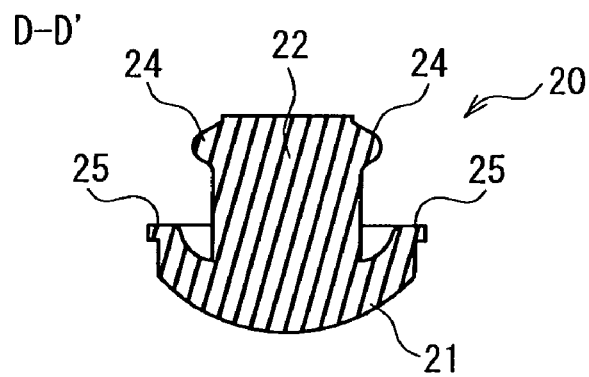
FIG. 5B is a cross-sectional view taken along a cut line D-D' in FIG. 5A.
Figure 5C:
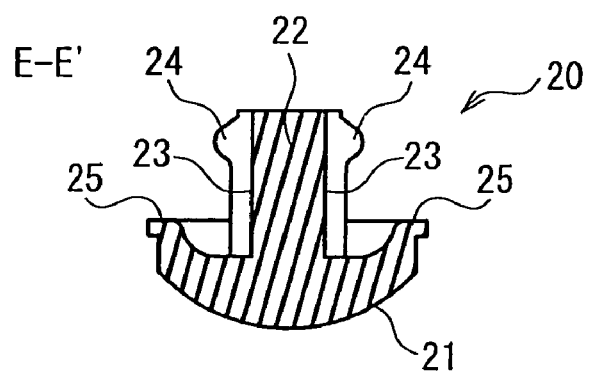
FIG. 5C is a cross-sectional view taken along a cut line E-E' in FIG. 5A.

FIG. 5 shows views illustrating a valve member constituting the flow control apparatus shown in FIG. 1, FIG. 5A is a top view, FIG. 5B is a cross-sectional view taken along a cut line D-D' in FIG. 5A, and FIG. 5C is a cross-sectional view taken along a cut line E-E' in FIG. 5A.

Figure 6:
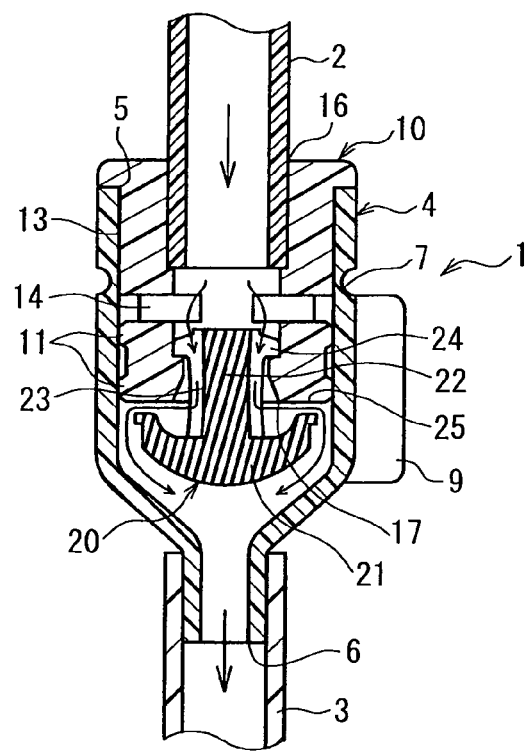
FIG. 6 is a cross-sectional view showing a state in which the valve member is opened in the flow control apparatus shown in FIG. 1.
Figure 7:
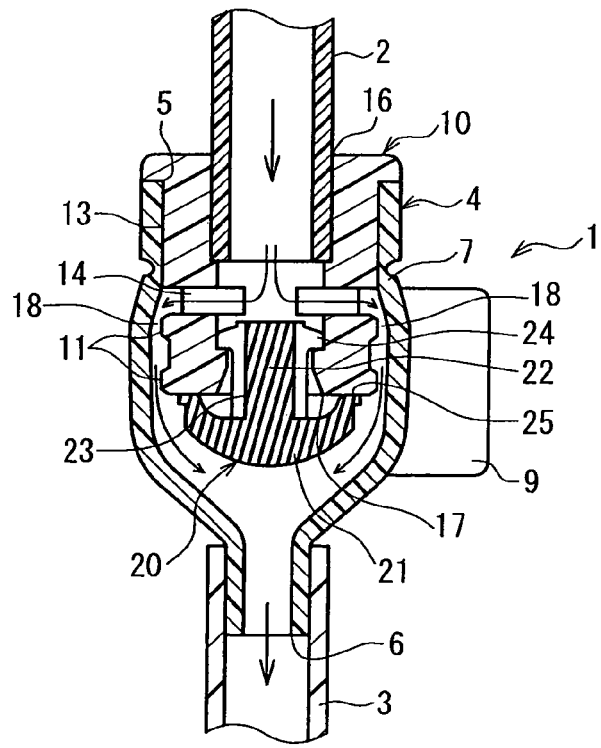
FIG. 7 is a cross-sectional view showing a state in which the outside member is deformed elastically in the flow control apparatus shown in FIG. 1.

FIG. 6 is a cross-sectional view showing a state in which the valve member is opened in the flow control apparatus shown in FIG. 1. FIG. 7 is a cross-sectional view showing a state in which the outside member is deformed elastically in the flow control apparatus shown in FIG. 1. Both of FIGS. 6 and 7 are cross-sectional views taken along the cut line A-A' in FIG. 1A in the same way as in FIG. 2A.

As shown in FIGS. 1A and 1B, a tube 2 for supplying a fluid and a tube 3 for discharging the fluid are attached to a flow control apparatus 1. The flow control apparatus 1 controls the flow of a fluid supplied from the tube 2. As used herein, "flow control" refers to the control of the flowing manner of a fluid.

Without the influence of an external force, the flow control apparatus 1 is configured so as to pass only a fluid supplied in an arrow direction (see FIG. 1B) at a set pressure or higher and so as not to pass a fluid supplied at a pressure lower than the set pressure. On the other hand, when an outside member 4 is deformed elastically by the external force, the flow control apparatus 1 passes also the fluid supplied at a pressure lower than the set pressure. This will be described specifically below.

As shown in FIGS. 2A and 2B, the flow control apparatus 1 includes the outside member 4, an inside member 10, and a valve member 20. The outside member 4 has a tubular shape, and includes an opening 5 on an upstream side and an opening 6 on a downstream side (see FIG. 3). Similarly, the inside member 10 also has a tubular shape, and includes an opening 16 on the upstream side and an opening 17 on the downstream side (see FIG. 4).

Furthermore, the inside member 10 is inserted in the outside member 4. The valve member 20 is placed at the opening 17 on the downstream side of the inside member 10. In Embodiment 1, the tube 2 is connected to the opening 16 on the upstream side of the inside member 10, and the tube 3 is connected to the opening 6 on the downstream side of the outside member 4.

Furthermore, as shown in FIGS. 2A and 2B, and FIGS. 4A and 4B, the inside member 10 includes a through-hole 14 and a first contact portion 11 that comes into contact with the outside member, which are disposed in this order in a direction (fluid flow direction) from the opening 16 on the upstream side to the opening 17 on the downstream side. The through-hole 14 passes through a side wall of the inside member 10 in a thickness direction. In FIG. 4B, "L1" represents the length from the through-hole 14 to the opening 17 on the downstream side of the inside member 10.

In Embodiment 1, two convex portions (ribs) 12 are formed along an outer periphery of the inside member 10. The cross-section of each convex portion 12 is formed in a trapezoidal shape, and top portions of the convex portions 12 form the first contact portion 11. Furthermore, a portion 13 positioned on the upstream side (on the opening 16 side) of the through-hole 14 in the inside member 10 is formed so as to come into contact with an inner surface of the outside member. The portion 13 functions as a second contact portion. In the subsequent description, the portion 13 will be referred to as the second contact portion 13.

Due to the above configuration, in Embodiment 1, when the inside member 10 is inserted in the outside member 4, the inside member 10 comes into contact with the inner surface of the outside member 4 by the first contact portion 11 and the second contact portion 13. Thus, as shown in FIGS. 2A and 2B, as long as the outside member 4 is not deformed, a fluid does not pass between the outside member 4 and the inside member 10.

In Embodiment 1, although two convex portions 12 are formed on the inside member 10, the number of the convex portions is not limited. The number of the convex portions 12 may be set in accordance with the sealing property required in the first contact portion 11. That is, if the sealing property between the outside member 4 and the first contact portion 11 is required to be increased as much as possible, the number of the convex portions 12 may be increased. On the other hand, if it is desired to easily release the contact between the first contact portion 11 and the outside member 4 (described later), the number of the convex portions 12 may be decreased. Furthermore, in Embodiment 1, although the cross-section of the convex portion 12 is formed in a trapezoidal shape, the cross-sectional shape of the convex portion 12 is not particularly limited. The cross-sectional shape of the convex portion may be a triangle or a semi-circle other than a trapezoid.

Furthermore, as shown in FIGS. 2A and 2B, and FIGS. 5A to 5C, the valve member 20 is configured so that only a fluid supplied at a set pressure or higher passes through the valve member 20 from the opening 16 on the upstream side of the inside member 10 to the opening 17 on the downstream side. In Embodiment 1, the valve member 20 includes an umbrella-shaped valve portion 21 and a protruding portion 22.

The valve portion 21 and the protruding portion 22 are integrally formed of a material excellent in elasticity, such as various kinds of rubber materials and various kinds of thermoplastic elastomers. Specifically, examples of the rubber material include natural rubber, isoprene rubber, butadiene rubber, styrene-butadiene rubber, nitryl rubber, chloroprene rubber, butyl rubber, acrylic rubber, ethylene-propylene rubber, hydrin rubber, urethane rubber, silicon rubber, and fluorine rubber. Examples of the thermoplastic elastomer include styrene-based, polyolefin-based, polyvinyl chloride-based, polyurethane-based, polyester-based, polyamide-based, polybutadiene-based, transpolyisoprene-based, fluorine rubber-based, and basic polyethylene-based thermoplastic elastomers. Furthermore, among them, silicon rubber is most preferred. Furthermore, the valve member 20 can be formed by molding.

The valve member 21 is formed so that it covers the opening 17 on the downstream side of the inside member 10, i.e., so that the diameter of the umbrella is larger than that of the opening 17. Furthermore, on the upstream side (reverse side of the umbrella) of the valve portion 21, an annular contact surface 25 is formed. Therefore, the valve portion 21 can come into contact with a surrounding region of the opening 17 of the inside member 10 to close the opening 17.

The protruding portion 22 is formed so as to protrude from a reverse side portion of the umbrella of the valve portion 21. Furthermore, as shown in FIG. 2, the protruding portion 22 is inserted from the opening 17 on the downstream side of the inside member 10 to the inside of the inside member 10, and furthermore, is fixed to the inside member 10 with the opening 17 on the downstream side closed with the valve portion 21.

Specifically, a projection 24 is formed on the surface of the protruding portion 22, and the projection 24 is hooked on a step 15 provided in the inside member 10, whereby the protruding portion 22 is fixed to the inside member 10. Furthermore, the positions of the projection 24 and the step 15 are adjusted so that the contact surface 25 of the valve portion 21 comes into contact with a surrounding region of the opening 17 of the inside member 10 when the projection is hooked on the step 15.

Furthermore, as shown in FIGS. 2A, 5A, and 5C, the projection 22 also is formed so that, when the protruding portion 22 is inserted in the inside member 10, a gap to be a flow path of a fluid is present between the inner surface of the inside member 10 and the projection 22. Specifically, the protruding portion 22 includes a concave portion 23 on a side surface, and the concave portion 23 forms a gap to be a flow path of a fluid.

Thus, the fluid supplied from the tube 2 passes through a gap between the concave portion 23 and the inner surface of the inside member 10, and thereafter, presses the valve portion 21. At this time, when the fluid is supplied at a set pressure or higher, as shown in FIG. 6, the closing by the valve member 21 is released by the elastic deformation of the protruding portion 21. Specifically, when a fluid is supplied at a set pressure or higher, the protruding portion 22 is deformed elastically in an extension direction to such a degree that the contact between the contact surface 25 of the valve portion 21 and the surrounding region of the opening 17 of the inside member 10 is released. Consequently, a fluid flows between the contact surface 25 of the valve portion 21 and the surrounding region of the opening 17 of the inside member 10.

Thus, in Embodiment 1, since the valve member 20 is attached to the inside member 10, only a fluid supplied at a set pressure or higher can pass through the flow control apparatus 1, and the passage of a fluid supplied at a pressure lower than the set pressure is inhibited. Furthermore, in the case where a fluid is supplied from a direction opposite to a direction of the arrows shown in FIG. 2, the valve portion 20 is pressed toward the opening 17 of the inside member, so that the contact between the contact surface 25 of the valve portion 21 and the surrounding region of the opening 17 of the inside member 10 becomes stronger. That is, the valve member 20 also functions as a check valve, and also inhibits the passage of a fluid from the direction opposite to the direction of the arrows shown in FIGS. 2A and 2B.

Furthermore, in Embodiment 1, the above-mentioned set pressure can be set by appropriately selecting the constituent material for the valve member 20, the cross-sectional area of a gap formed between the concave portion 23 and the inner surface of the inside member 10, etc. The magnitude of the set pressure may be determined depending upon the use of the flow control apparatus 1 and the pressure of a pump. The transfusion pump and the syringe pump may have a function of issuing a warning when the internal pressure of the injection circuit reaches a predetermined value or more. In this case, it is necessary to adjust the above-mentioned set pressure so that a warning is not issued.

If a fluid cannot pass through the flow control apparatus 1 unless the pressure of the fluid is a set pressure or higher, priming based on a head pressure becomes difficult when the flow control apparatus 1 is incorporated in a transfusion circuit (see FIG. 8 described later) or a drug injection circuit (see FIG. 9 described later). Therefore, as shown in FIG. 7, the outside member 4 (see FIG. 3) is formed so as to be deformed elastically by an external force, thereby forming a gap 18 communicating with the through-hole 14 between the outside member 4 and the first contact portion 11.

At this time, the gap 18 and the through-hole 14 form a new flow path without passing through the valve member 20, so that a fluid supplied at a pressure lower than a set pressure can pass through the flow control apparatus 1. Thus, in the case where the flow control apparatus 1 is incorporated in an injection circuit for the process of transfusing and the administration of a drug, priming can be performed by a head pressure.

Furthermore, in Embodiment 1, the external force causing the outside member 4 to be deformed elastically is given by a user. In Embodiment 1, the magnitude of a presumed external force is such a degree as that applied by a human generally. In order to enhance the operability by a user, i.e., in order to facilitate the addition of an external force to the outside member 4 by a user, operation portions 8 and 9 are provided on an outer surface of the outside member 4 (see FIGS. 1A and 1B).

Specifically, the operation portions 8 and 9 are members that protrude from the outer surface of the outside member 4 and are provided on a portion other than a portion 4a which is in contact with the second contact portion 13 of the inside member 10, i.e., a portion 4b (see FIG. 3). A user can deform the outside member 4 elastically merely by putting the operation portions 8 and 9 between fingers and moving them respectively in the directions of the arrows V and W shown in FIG. 1A. Furthermore, in Embodiment 1, the operation portions 8 and 9 are formed in a wing shape so that the user can put them between the fingers easily, and each vane is placed in parallel to the flow direction of a fluid.

Furthermore, in Embodiment 1, a groove 7 is formed along an outer periphery of the outside member 4 between the portions 4a and 4b on the outer surface of the outside member 4. Thus, when the user applies an external force to the operation portions 8 and 9, the outside member 4 is elastically deformed more greatly in the portion 4b (see FIG. 3) than in the portion 4a with the groove 7 as a boundary. Therefore, according to Embodiment 1, even if the outside member 4 is deformed elastically, the contact between the second contact portion 13 of the inside member and the outside member 4 is ensured, and the leakage of a fluid from between the outside member 4 and the inside member 10 is suppressed.

In Embodiment 1, an angle formed by the operation portions 8 and 9 when the flow control apparatus 1 is viewed from above is not particularly limited. The angle formed by the operation portions 8 and 9 may be set appropriately considering the size of the outside member 4. The number of the operation portions 8 and 9 is not particularly limited, either, and can be set appropriately considering the operability of the user. Furthermore, the shape of the operation portions 8 and 9 may be those other than a wing shape.

Furthermore, the constituent material for the inside member 10 is preferably a material that has an elastic modulus smaller than that of the constituent material for the outside member 4 and is unlikely to be deformed elastically in order to ensure the contact between the second contact portion 13 and the outside member 4 at a time of elastic deformation of the outside member 4. In Embodiment 1, examples of the constituent material for the outside member 4 include those which have excellent elasticity such as the material similar to that of the above-mentioned valve member 20, i.e., various kinds of rubber materials and various kinds of thermoplastic elastomers. Furthermore, examples of the constituent material for the inside member 10 include a polypropylene (PP) resin, a polycarbonate resin, an ABS resin, a polyethylene terephthalate (PET) resin, and a polybutylene terephthalate (PBT) resin.

Furthermore, among the above-mentioned materials, a polyvinyl chloride-based thermoplastic elastomer and a polybutadiene-based thermoplastic elastomer preferably are used as the constituent material for the outside member 4, and a polycarbonate resin is preferably used as the constituent material for the inside member 10.

Next, the injection circuit in Embodiment 1 will be described with reference to FIGS. 8 to 10.

The injection circuit in Embodiment 1 includes the flow control apparatus 1 in Embodiment 1 described using FIGS. 1 to 7. The injection circuit in Embodiment 1 can be used as, for example, a transfusion circuit, a drug injection circuit, or a blood-collecting circuit (A line) used in an invasive blood pressure measurement method. This will be described below. In FIGS. 8 to 10, elements denoted with the reference numerals used in FIGS. 1 to 7 are shown as the same elements denoted with the corresponding reference numerals in FIGS. 1 to 7.

Figure 8:
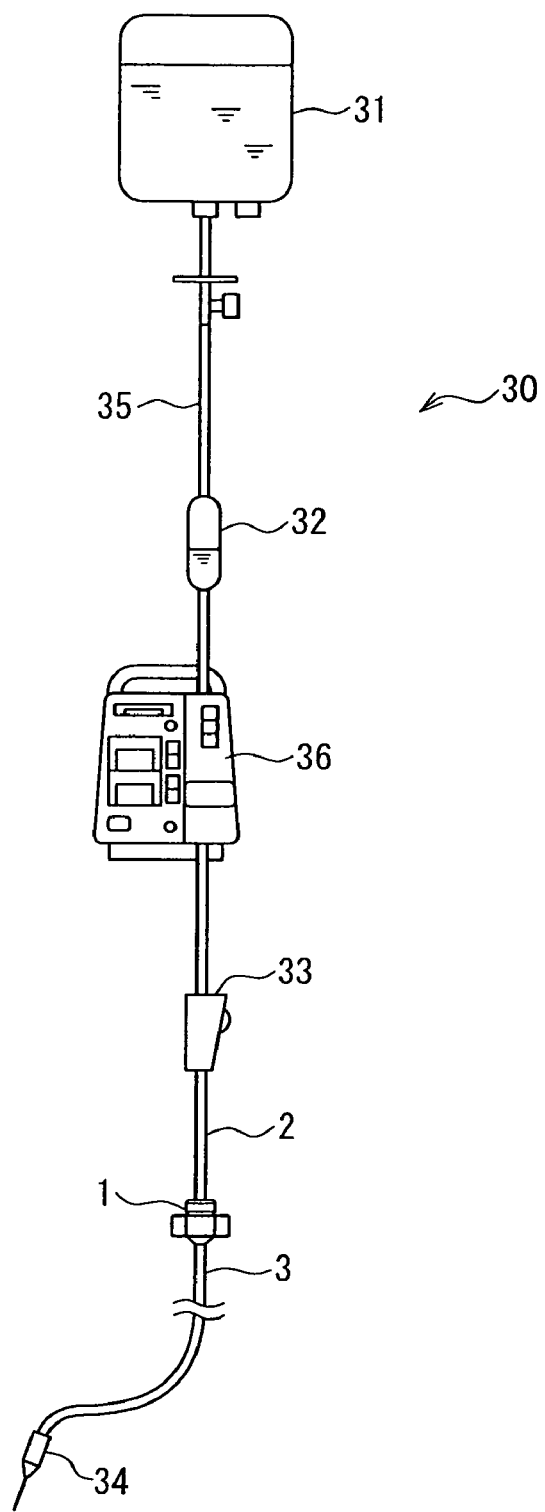
FIG. 8 is a view showing an example using the injection circuit in Embodiment 1 as a transfusion circuit.

FIG. 8 is a view showing an example in which the injection circuit in Embodiment 1 is used as a transfusion circuit. As shown in FIG. 8, a transfusion circuit 30 includes a transfusion bag 31, a drip chamber 32, a clamp 33, a flow control apparatus 1, and a puncture needle 34. Furthermore, a tube 2 connected to an inflow side of the flow control apparatus 1 is connected to the drip chamber 32. Furthermore, a transfusion pump 36 and the clamp 33 are attached in this order to the tube 2 in a flow direction of a transfusion. Furthermore, a tube 3 connected to a discharge side of the flow control apparatus 1 is connected to the puncture needle 34. A tube 35 connects the drip chamber 32 to the transfusion bag 31.

In this manner, if the flow control apparatus 1 is used for the transfusion circuit 30, the transfusion does not flow beyond the flow control apparatus 1 even when the transfusion pump 36 is removed while the damp 33 is omitted to be closed (is opened), so that the occurrence of free-flow is suppressed. Furthermore, in the case where priming is performed by a head pressure, the outside member 4 is deformed elastically as shown in FIG. 7, whereby the transfusion can pass through the flow control apparatus 1, so that priming can be completed while the flow control apparatus 1 is attached.

In the example shown in FIG. 8, although the flow control apparatus 1 is placed on a downstream side of the clamp 33, the present invention is not limited to the example. The flow control apparatus 1 also can be placed at a position between the transfusion pump and the drip chamber 32.

Figure 9:
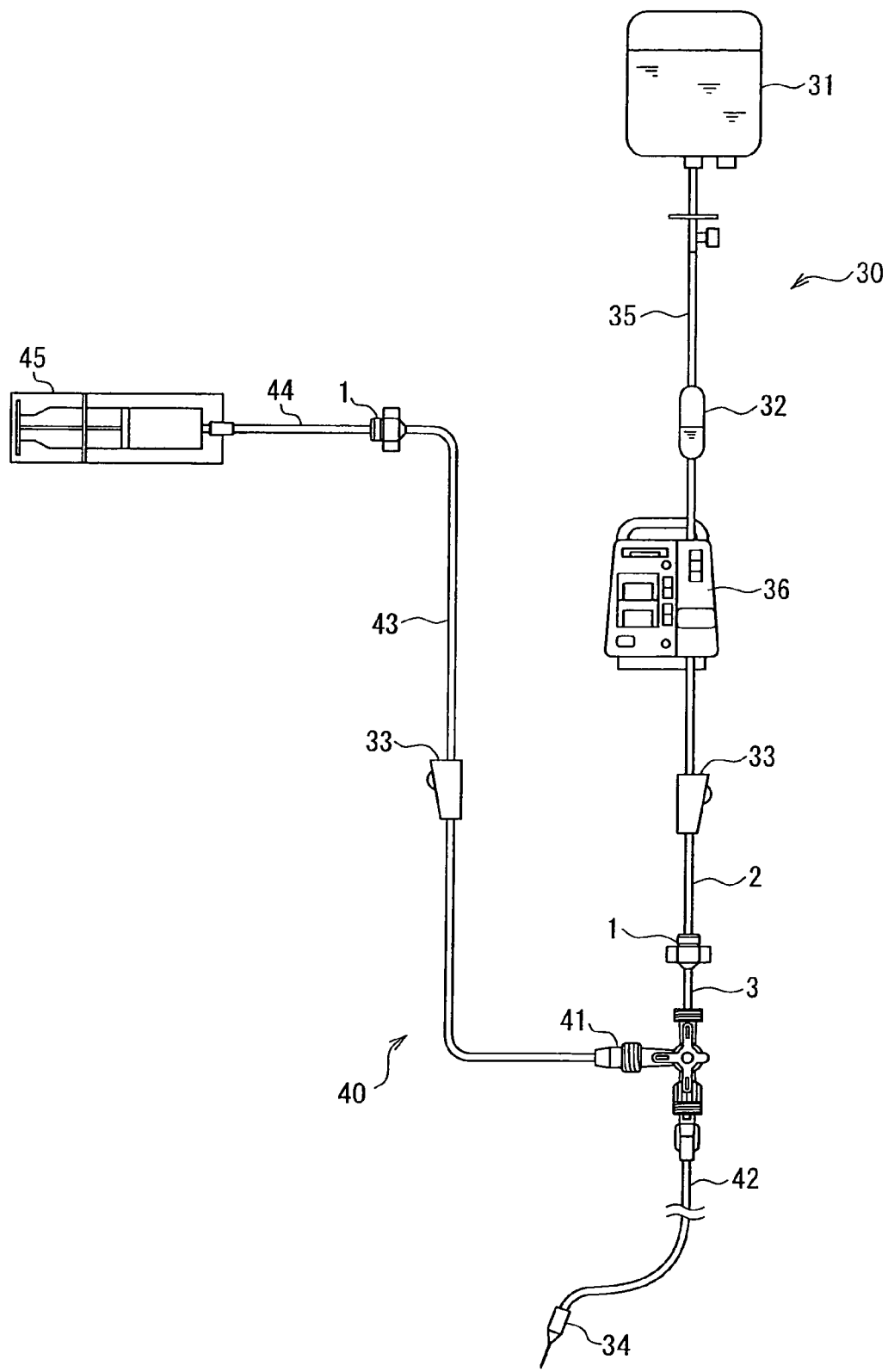
FIG. 9 is a view showing an example using the injection circuit in Embodiment 1 as a drug injection circuit.

FIG. 9 is a view showing an example in which the injection circuit in Embodiment 1 is used as a drug injection circuit. The injection circuit shown in FIG. 9 includes both a drug injection circuit 40 and the transfusion circuit 30, and the drug injection circuit 40 and the transfusion circuit 30 are connected to each other via a three-way cock 41. Therefore, in the injection circuit shown in FIG. 9, the injection of a transfusion and the administration of a drug can be performed simultaneously. Furthermore, in the injection circuit shown in FIG. 9, the administration of a drug also can be performed intermittently while the injection of a transfusion is performed. Furthermore, as shown in FIG. 9, the drug injection circuit 40 includes the flow control apparatus 1 in Embodiment 1, in the same way as in the transfusion circuit 30. Furthermore, a syringe pump 45 is connected to the drug injection circuit 40.

Specifically, the drug injection circuit 40 includes the flow control apparatus 1, a tube 44 connected to an inflow side of the flow control apparatus 1, and a tube 43 connected to a discharge side. The syringe pump 45 is connected to the tube 44. Furthermore, a syringe set at the syringe pump 45 is filled with drugs required to be administered in a small amount, such as an anticancer agent, an antibiotic, a fat emulsion, and a tranquilizer. The clamp 33 is attached to the tube 43 so as to enhance operability. The transfusion circuit 30 is the same as that shown in FIG. 8, and includes the flow control apparatus 1.

Furthermore, the tube 3 on a discharge side of the flow control apparatus 1 of the transfusion circuit 30 is connected to one of opposed ports of the three-way cock 41, and the puncture needle 34 is connected to the other of the opposed ports via a tube 42. The tube 43 of the drug injection circuit 40 is connected to the remaining port of the three-way cock 41.

Thus, in the injection circuit shown in FIG. 9, the injection of a transfusion and the administration of a drug can be performed simultaneously or the administration of a drug can be performed intermittently while the injection of a transfusion is performed by switching a handle of the three-way cock 41. Furthermore, as described above, the drug injection circuit 40 includes the flow control apparatus 1. Therefore, even if the syringe comes off a pump body in the syringe pump 45, the administration of a drug in an amount more than necessary is inhibited by the flow control apparatus 1. The flow control apparatus 1 also can suppress the occurrence of free flow in the administration of a drug using the syringe pump 45.

Furthermore, in the same way as in the example shown in FIG. 8, the outside member 4 is deformed elastically (see FIG. 7), whereby priming in the drug injection circuit 40 can be performed easily. In the drug injection circuit 40, priming also can be performed using a fast-forward function of the syringe pump 45.

Figure 10:
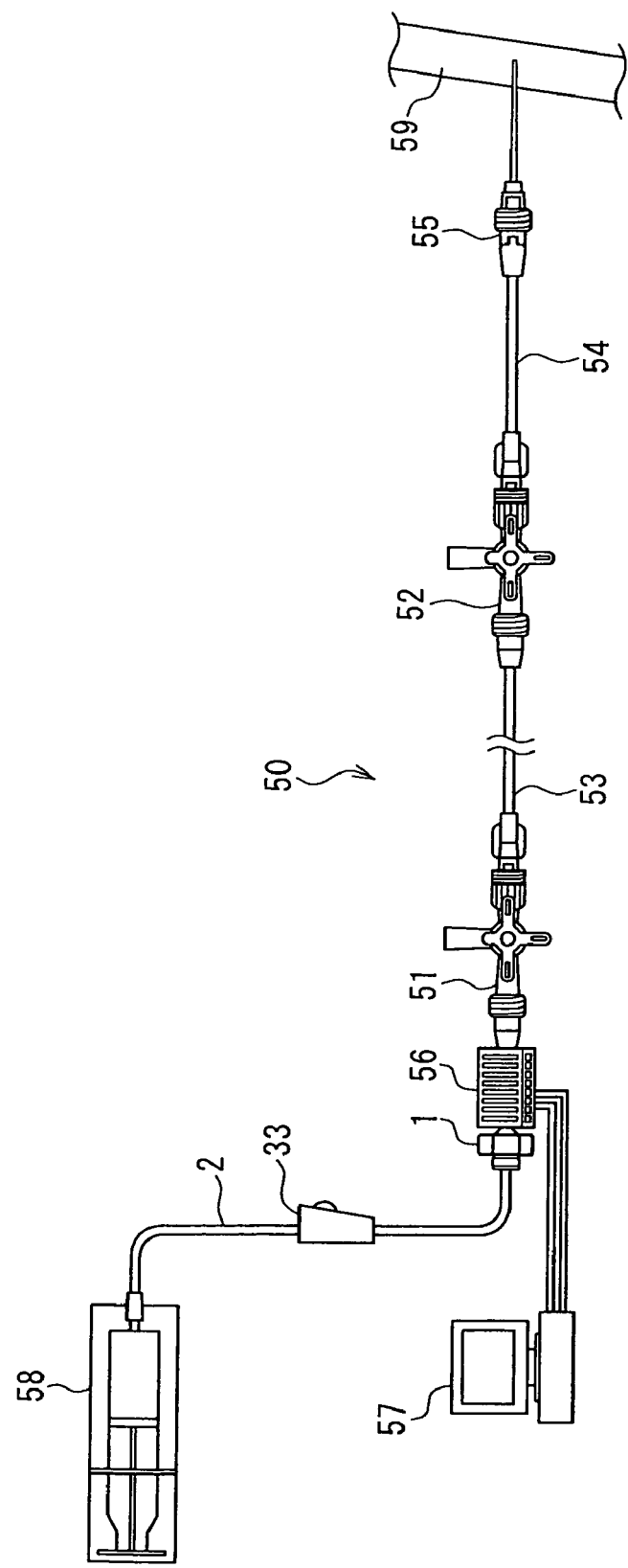
FIG. 10 is a view showing an example using the injection circuit in Embodiment 1 as a blood-collecting circuit.

FIG. 10 is a view showing an example in which the injection circuit in Embodiment 1 is used as a blood-collecting circuit. As shown in FIG. 10, a blood-collecting circuit 50 is used in an invasive blood pressure measurement method. The blood-collecting circuit 50 includes the flow control apparatus 1, a blood pressure transducer 56, mixed injection ports 51 and 52, and a puncture needle 55. The puncture needle 55 is kept in an artery 59 of a patient.

In the blood-collecting circuit 50, the blood pressure transducer 56 and the puncture needle 55 are connected to each other via the mixed injection port 51, a tube 53, the mixed injection port 52, and a tube 54. Furthermore, the discharge side of the flow control apparatus 1 is connected directly to the blood pressure transducer 56. The tube 2 connected to an inflow side of the flow control apparatus 1 is connected to a syringe pump 58. A syringe in the syringe pump 58 is filled with physiological saline. Furthermore, the clamp 33 is attached to the tube 2 so as to enhance the operability.

Furthermore, in the blood-collecting circuit 50, the flow path from the blood pressure transducer 56 to the puncture needle 55 is filled with a physiological saline. Thus, the blood pressure of blood flowing through the artery 59 is transmitted to the blood pressure transducer 56 via the physiological saline filling the flow path. The blood pressure transducer 56 outputs an electric signal in accordance with the level of the transmitted blood pressure to a computer 57. When the blood pressure transducer 56 outputs an electric signal, the computer 57 displays a measurement value (blood pressure value) specified by the electric signal on a screen.

Furthermore, during the measurement of a blood pressure, the physiological saline is supplied to the flow path from the blood pressure transducer 56 to the puncture needle 55 by the syringe pump 58 at a constant flow rate (for example, 3 ml/h). Furthermore, an anticoagulant is added to the physiological saline filling the syringe of the syringe pump 58. The purpose of this is to suppress the flowing blood from being coagulated in the puncture needle 55, which makes it impossible to perform blood measurement in the case where blood flows from the artery 59 to the puncture needle 55.

An example of the anticoagulant includes heparin. In the example shown in FIG. 10, the physiological saline filling the syringe of the syringe pump 58 is a physiological saline with heparin added thereto. In the subsequent description, the physiological saline filling the syringe of the syringe pump 58 will be referred to as a heparin-added physiological saline.

Furthermore, before the commencement of blood measurement, the flow path from the blood pressure transducer 56 to the puncture needle 55 is previously filled with a heparin-added physiological saline by the syringe pump 58. In the example shown in FIG. 10, the flow path is filled with the heparin-added physiological saline, using the fast-forward function of the syringe pump 58.

In the example shown in FIG. 10, when the syringe in the syringe pump 58 comes off the pump body during blood measurement, it becomes difficult to supply the heparin-added physiological saline at a constant flow rate. At this time, assuming that the flow control apparatus 1 is not attached, the heparin-added physiological saline is supplied by a head pressure. Then, in the case where the head pressure is lower than the blood pressure, the blood flows in the flow path. Furthermore, in the case where the head pressure is higher than the blood pressure, there is a possibility that a great amount of an anticoagulant (heparin in the example shown in FIG. 10) may be injected into the artery 59 of the patient. Furthermore, if the syringe comes off the pump body in the case where the flow control apparatus 1 is not attached, the transmitted pressure escapes to the syringe pump 58 side, which decreases the measurement precision in blood measurement.

In order to avoid such a problem, in Embodiment 1, the flow control apparatus 1 is attached as shown in FIG. 10. That is, in the example shown in FIG. 10, the flow control apparatus 1 suppresses the backflow of the blood to the flow path, the inflow of the anticoagulant (heparin in the example shown in FIG. 10) to a human body, and the decrease in measurement precision in the case where the syringe pump comes off the pump body.

In the blood-collecting circuit 50, the mixed injection ports 51 and 52 are used in the case where blood is collected during the measurement of a blood pressure. Specifically, first, a negative pressure is applied by a syringe (not shown) connected to the mixed injection port 51 at a position away from the puncture needle 55, whereby blood is allowed flow to the flow path. Then, the flowing blood is collected by a syringe (not shown) connected to the mixed injection port 52 at a position close to the puncture needle 55. After the blood is collected, the flow path is washed using the fast-forward function of the syringe pump 58.

In the example shown in FIG. 10, a transfusion bag and a transfusion pump also can be used in place of the syringe pump 58. In this case, the flow path is filled with a heparin-added physiological saline by elastically deforming the outside member 4 and using a head pressure, as shown in FIG. 7.

Embodiment 2

Figure 11A:
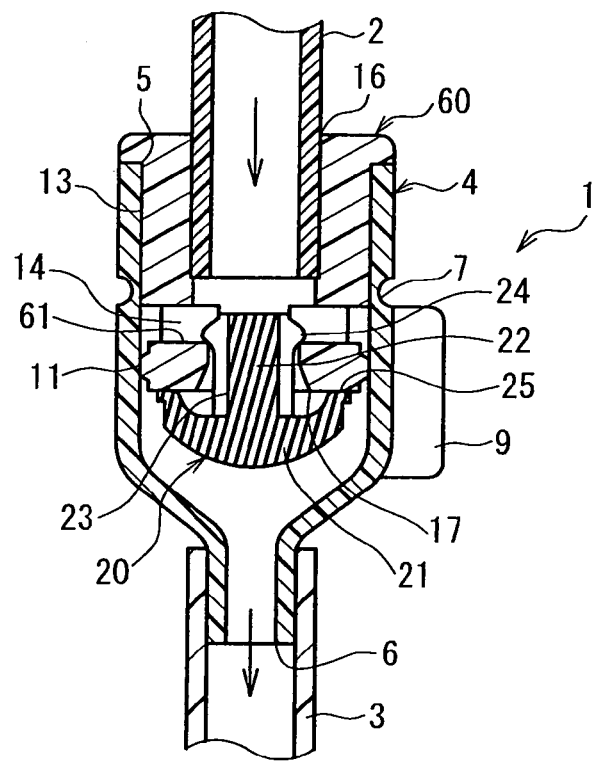
FIG. 11 shows cross-sectional views illustrating a cross-sectional configuration of a flow control apparatus in Embodiment 2 of the present invention, and FIGS. 11A and 11B respectively show cross-sections in different cut directions.
Figure 11B:
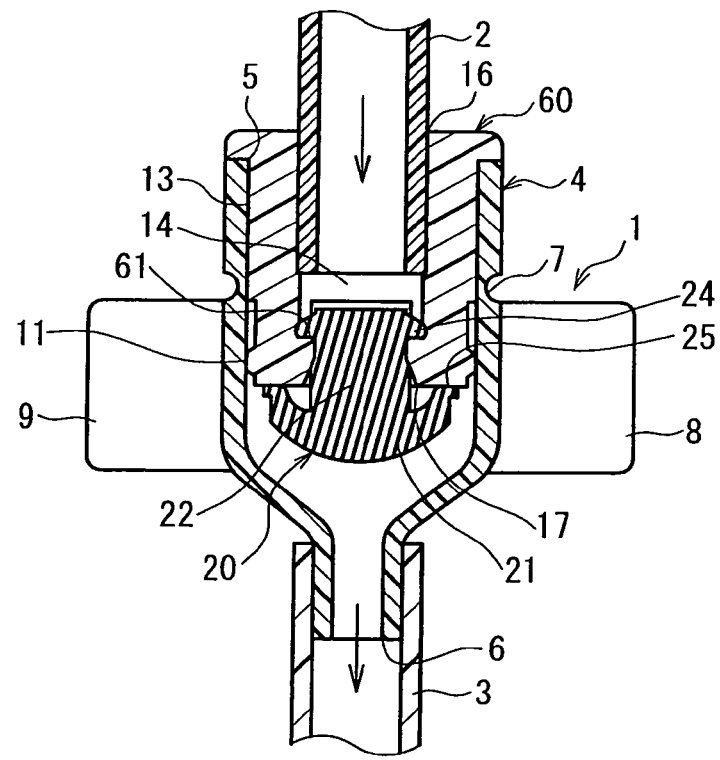
Figure 12A:
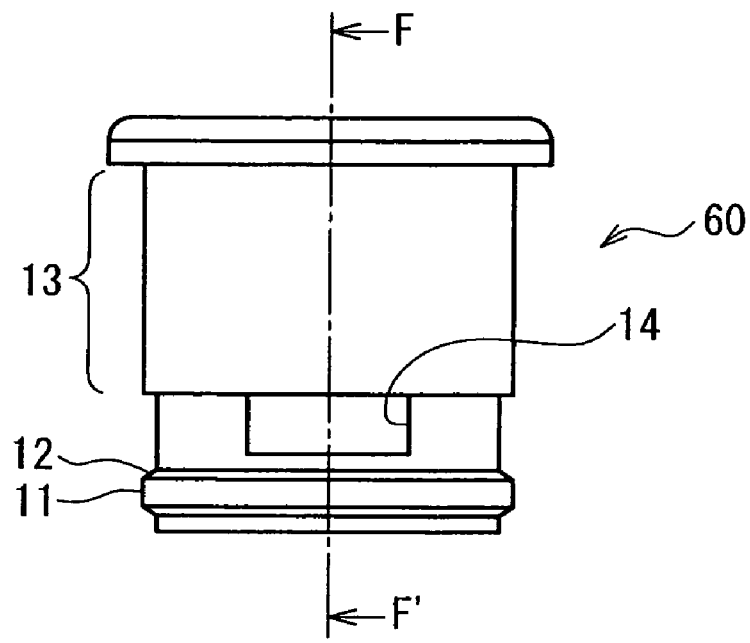
FIG. 12A is a side view.
Figure 12B:
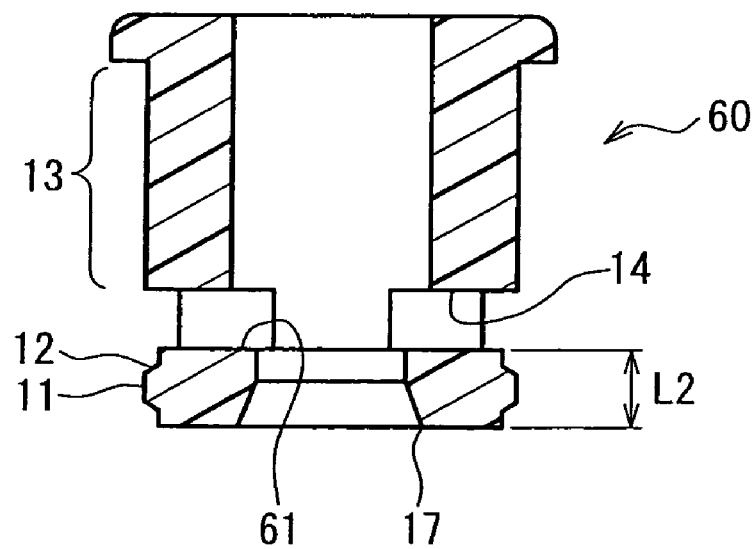
FIG. 12B is a cross-sectional view taken along a cut line F-F' in FIG. 12A.

Next, a flow control apparatus and an injection circuit in Embodiment 2 of the present invention will be described with reference to FIGS. 11 and 12. FIG. 11. FIG. 11 shows cross-sectional views illustrating a cross-sectional configuration of the flow control apparatus in Embodiment 2 of the present invention, and FIGS. 11A and 11B respectively show cross-sections in different cut directions. FIG. 12 shows views illustrating an inside member constituting the flow control apparatus shown in FIG. 11, FIG. 12A is a side view, and FIG. 12B is a cross-sectional view taken along a cut line F-F' in FIG. 12A.

The outer appearance of the flow control apparatus in Embodiment 2 is the same as that of the flow control apparatus in Embodiment 1 shown in FIG. 1. FIG. 11A corresponds to a cross-sectional view taken along a cut line A-A' in FIG. 1, and FIG. 11B corresponds to a cross-sectional view taken along a cut line B-B' in FIG. 1A. Furthermore, in FIGS. 11 and 12, elements denoted with the reference numerals used in FIGS. 1 to 7 are shown as the same elements denoted with the corresponding reference numerals in FIGS. 1 to 7.

As shown in FIGS. 11A, 11B, 12A, and 12B, the flow control apparatus in Embodiment 2 is different from the flow control apparatus (see FIG. 2) in Embodiment 1 in the configuration of an inside member 60. The flow control apparatus in Embodiment 2 is configured in the same way as in the flow control apparatus in Embodiment 1 in the other configurations. Furthermore, the injection circuit in Embodiment 2 has the flow control apparatus in Embodiment 2. The injection circuit in Embodiment 2 also can be used as, for example, a transfusion circuit, a drug injection circuit, or a blood-collecting circuit (A line) used in an invasive blood pressure measurement method. Hereinafter, the difference will be described specifically.

As shown in FIGS. 11A and 11B, in Embodiment 2, the through-hole 14 of the inside member 60 is formed so that an opening thereof is placed at a position facing the protruding portion 22 of the valve member 20 attached to the inside member 60, unlike Embodiment 1. Furthermore, as shown in FIG. 12B, in Embodiment 2, a length L2 from the through-hole 14 of the inside member 60 to the opening 17 on the downstream side is smaller than the length L1 (see FIG. 4B) from the through-hole 14 of the inside member 10 to the opening 17 on the downstream side. Furthermore, the projection 24 of the protruding portion 22 is fixed to the inside member 60 by being hooked on an inner wall 61 of the through-hole 14.

Due to the configuration of the inside member 60, according to Embodiment 2, when the outside member 4 is deformed elastically to perform priming, the amount of air accumulated in the vicinity of the projection 24 can be decreased compared with that in Embodiment 1. Therefore, when a fluid is fed at a set pressure after the completion of priming, the amount of bubbles to be mixed in the tube 3 can be decreased. Consequently, according to the transfusion circuit and the drug injection circuit constituted by using the flow control apparatus in Embodiment 2, the safety of a patient can be enhanced further.

Furthermore, even in Embodiment 2, only a fluid supplied at a set pressure or higher can pass through the flow control apparatus and the passage of a fluid supplied at a pressure lower than the set pressure can be inhibited in the same way as in Embodiment 1. Furthermore, as described above, the elastic deformation of the outside member 4 can form a flow path, which allows a fluid at the set pressure or lower to flow.

In Embodiment 2, as described above, since the length L2 from the through-hole 14 of the inside member 60 to the opening 17 on the downstream side is smaller than that in Embodiment 1, the number of the convex portions 12 is one as shown in FIGS. 12A and 12B. Even in Embodiment 2, the number of the convex portions 12 is not limited in the same way as in Embodiment 1. Furthermore, the constituent material for the inside member 10 described in Embodiment 1 also can be used as the constituent material for the inside member 60.

Embodiment 3

Figure 13A:
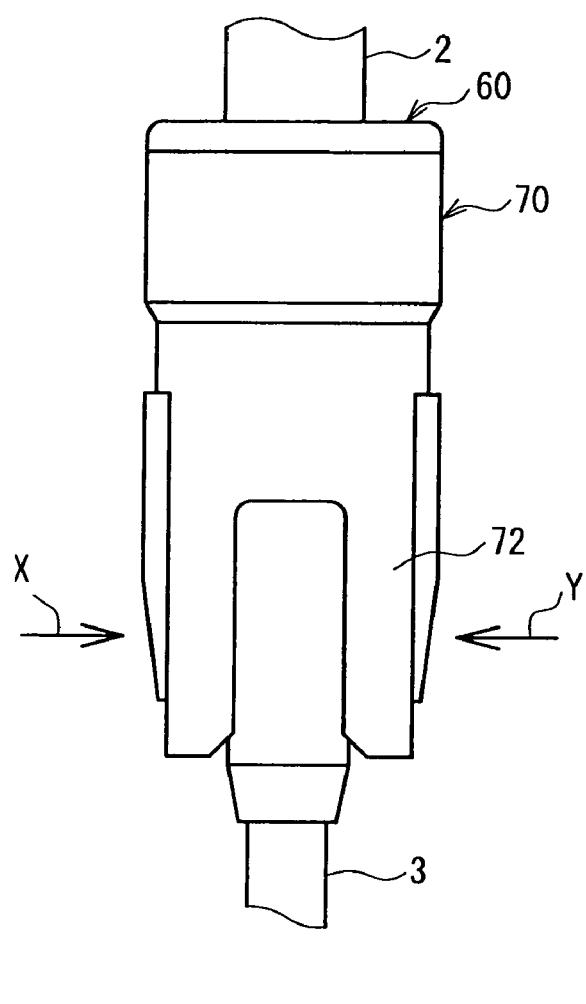
FIGS. 13A and 13B are viewed in different directions. Furthermore, the viewing direction in FIG. 13A is perpendicular to the viewing direction in FIG. 13B.
Figure 13B:
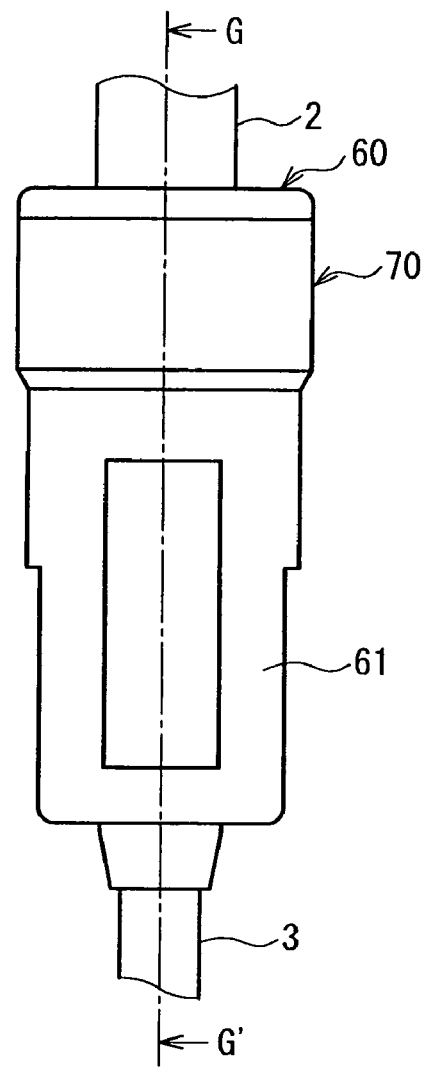
Figure 14A:
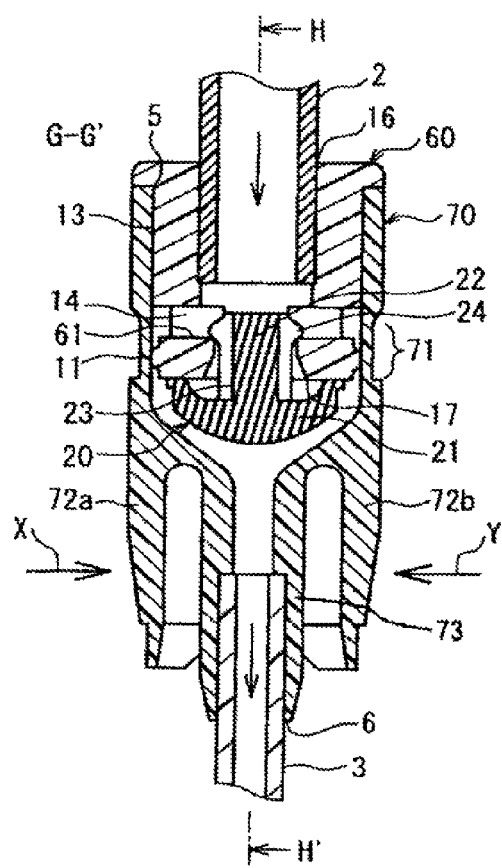
FIG. 14A is a cross-sectional view taken along a cut line G-G' in FIG. 13B.
Figure 14B:
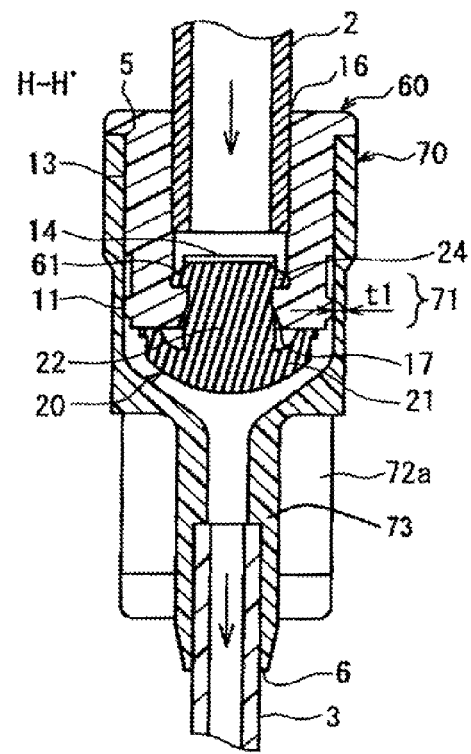
FIG. 14B is a cross-sectional view taken along a cut line H-H' in FIG. 14A.

Next, the flow control apparatus and the injection circuit in Embodiment 3 of the present invention will be described with reference to FIGS. 13 and 14. FIG. 13 shows views illustrating an outer appearance of the flow control apparatus in Embodiment 3 of the present invention, and FIGS. 13A and 13B are viewed in different directions. Furthermore, the viewing direction in FIG. 13A is perpendicular to the viewing direction in FIG. 13B. FIG. 14 shows cross-sectional views illustrating a configuration of the flow control apparatus shown in FIG. 13, FIG. 14A is a cross-sectional view taken along a cut line G-G' in FIG. 13B, and FIG. 14B is a cross-sectional view taken along a cut line H-H' in FIG. 14A.

As shown in FIGS. 13 and 14, the flow control apparatus in Embodiment 3 includes the valve member 20, the inside member 60, and an outside member 70, and the outside member 70 is different from those shown in Embodiments 1 and 2. In FIGS. 13 and 14, elements denoted with the reference numerals used in FIGS. 11 and 12 are shown as the same elements denoted with the corresponding reference numerals in FIGS. 11 and 12.

As shown in FIGS. 14A and 14B, a portion 73 on a downstream side of the outside member 70 has a small diameter. The tube 3 is inserted in the small-diameter portion (hereinafter, referred to as a "nozzle portion") 73. Furthermore, in the outside member 70, a portion on a downstream side of a portion in contact with the first contact portion 11 is provided with operation portions 72a and 72b. The operation portions 72a and 72b are a pair of members that protrude toward the downstream side, unlike the operation portions 8 and 9 in Embodiments 1 and 2. Furthermore, the operation portions 72a and 72b are placed so as to be opposed to each other with the nozzle portion 73 interposed therebetween.

The outside member 70 has a thin portion 71 in a region other than the portion in contact with the second contact portion 13 (in Embodiment 3, a region between the portion in contact with the second contact portion 13 and the operation portions 72a and 72b). The thin portion 71 is formed so that the thickness thereof is smaller than that of the portion in contact with the second contact portion 13 and is easily deformed elastically. Furthermore, the inside member 60 is placed so that each position of the through-hole 14 is matched with the position of the operation portion 72a or the operation portion 72b.

Due to the above configuration, when the operation portions 72a and 72b are moved respectively in directions of arrows X and Y in FIGS. 13A and 14A, the thin portion 71 in the vicinity of base ends of the operation portions 72a and 72b is elastically deformed outward. Then, a gap similar to the gap 18 shown in FIG. 7 in Embodiment 1 is formed between the outside member 70 and the first contact portion 11. Consequently, even in Embodiment 3, a new flow path without passing through the valve member 20 is formed, and priming can be performed by a head pressure in the same way as in Embodiments 1 and 2.

Furthermore, in Embodiment 3, a thickness t1 of the thin portion 71 may be determined considering the constituent material for the outside member 70 so that the outside member 70 is easily deformed elastically when an external force is applied by a user. For example, if the outside member 70 is formed of a polyvinyl chloride based thermoplastic elastomer, a polybutadiene based thermoplastic elastomer, polyethylene, or polypropylene, the thickness t1 may be set to be about 0.1 mm to 1 mm.

Even in the flow control apparatus in Embodiment 3, when the outside member 70 is not deformed elastically, only a fluid supplied at a set pressure or higher can pass through the flow control apparatus, and the passage of a fluid supplied at a pressure lower than the set pressure is inhibited, in the same way as in Embodiments 1 and 2. Furthermore, the injection circuit in Embodiment 3 includes the flow control apparatus in Embodiment 3. The injection circuit in Embodiment 3 also can be used as, for example, a transfusion circuit, a drug injection circuit, or a blood-collecting circuit (A line) used in an invasive blood pressure measurement method.

Embodiment 4

Figure 15A:
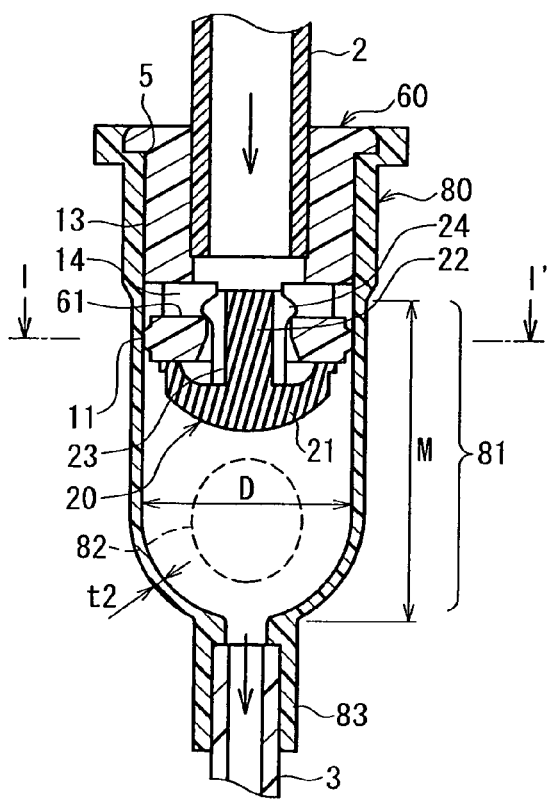
FIG. 15 shows cross-sectional views illustrating a configuration of a flow control apparatus in Embodiment 4 of the present invention, and FIGS. 15A and 15B respectively show cross-sections in different cut directions. The viewing direction in FIG. 15A is perpendicular to the viewing direction in FIG. 15B.
Figure 15B:
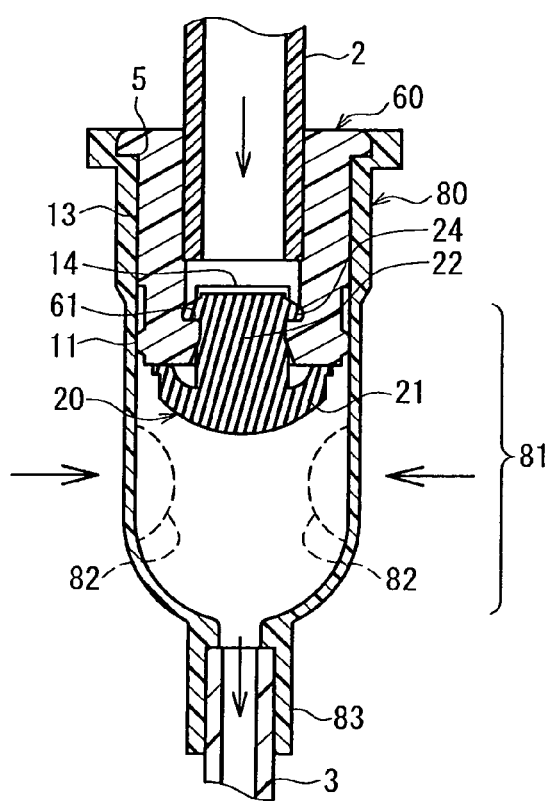
Figure 16A:
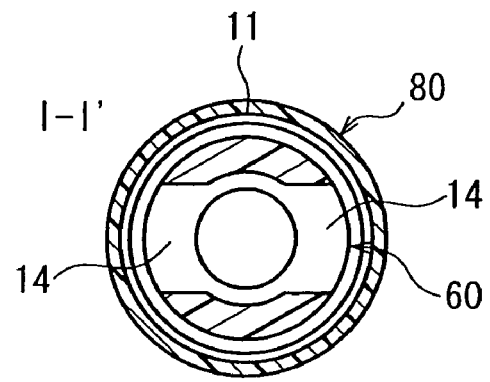
FIG. 16A shows a state in which an outside member is not deformed elastically.
Figure 16B:
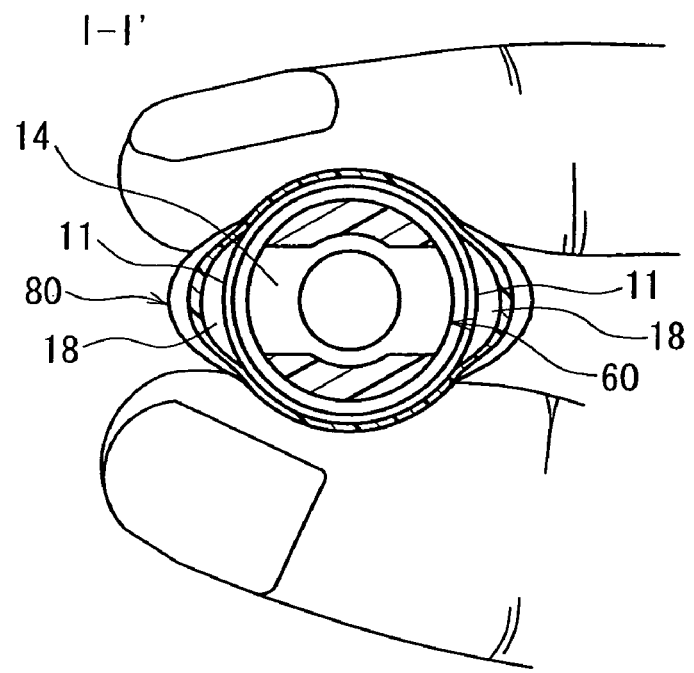
FIG. 16B shows a state in which the outside member is deformed elastically.

Next, a flow control apparatus and an injection circuit in Embodiment 4 of the present invention will be described with reference to FIGS. 15 and 16. FIG. 15 shows cross-sectional views illustrating a configuration of the flow control apparatus in Embodiment 4 of the present invention, and FIGS. 15A and 15B respectively show cross-sections in different cut directions. The cut direction in FIG. 15A is perpendicular to the cut direction in FIG. 15B. FIG. 16 shows cross-sectional views taken along a cut line I-I' in FIG. 15A, FIG. 16A shows a state in which the outside member is not deformed elastically, and FIG. 16B shows a state in which the outside member is deformed elastically.

As shown in FIG. 15, the flow control apparatus in Embodiment 4 includes the valve member 20, the inside member 60, and an outside member 80, and the outside member 80 is different from those shown in Embodiments 1 to 3. In FIGS. 15 and 16, elements denoted with the reference numerals used in FIGS. 11 and 12 are shown as the same elements denoted with the corresponding reference numerals in FIGS. 11 to 12.

As shown in FIGS. 15A and 15B, even in Embodiment 4, a portion 83 on a downstream side of the outside member 80 has a small diameter and the tube 3 is inserted in the small-diameter portion (nozzle portion) 83 in the same way as in Embodiment 3. Furthermore, even in Embodiment 4, the outside member 80 includes a thin portion 81 in a region other than a portion in contact with the second contact portion 13 in the same way as in Embodiment 3.

In Embodiment 4, an entire region between the portion in contact with the second contact portion 13 and the nozzle portion 83 in the outside member 80 forms the thin portion 81, unlike Embodiment 3. Furthermore, in Embodiment 4, although operation portions are not provided on the outside member 80 unlike Embodiments 1 to 3, the area of the thin portion 81 is large, so that a user can easily deform the outside member 80 elastically.

As shown in FIGS. 16A and 16B, the user can form a gap (see FIG. 7) between the outside member 80 and the first contact portion 11 by pressing a region 82 (see FIG. 15A) not overlapping the openings of the through-hole 14 in a radial direction of the outside member 80. Consequently, even in Embodiment 4, a new flow path without passing through the valve member 20 is formed, and priming can be performed by a head pressure in the same way as in Embodiments 1 and 2. Thus, according to Embodiment 4, the outside member 80 easily can be deformed elastically without providing operation portions on the outside member 80, unlike Embodiments 1 to 3. The production cost of the outside member 80 can be reduced.

Furthermore, even in Embodiment 4, a thickness t2 of the thin portion 81 may be determined considering the constituent material for the outside member 80. For example, if the outside member 80 is formed of a polyvinyl chloride based thermoplastic elastomer, a polybutadiene based thermoplastic elastomer, polyethylene, or polypropylene, the thickness t2 may be set to be about 0.1 mm to 1 mm.

Furthermore, in Embodiment 4, in order to ensure the area of the thin portion 81, it is preferred that the thin portion 81 has a cylindrical shape or a conical shape satisfying the following condition. That is, assuming that a length from an end on an upstream side of the thin portion 81 to an end on a downstream side thereof in a center axis direction (flow direction) of the outside member 80 is M, and a maximum inner diameter in the thin portion 81 is D, it is preferred that a ratio (M/D) of the length M with respect to the maximum inner diameter D is 1 to 5.

Even in the flow control apparatus in Embodiment 4, when the outside member 80 is not deformed elastically, only a fluid supplied at a set pressure or higher can pass through the flow control apparatus and the passage of a fluid supplied at a pressure lower than the set pressure is inhibited in the same way as in Embodiments 1 and 2. Furthermore, the injection circuit in Embodiment 4 includes the flow control apparatus in Embodiment 4. The injection circuit in Embodiment 4 also can be used as, for example, a transfusion circuit, a drug injection circuit, or a blood-collecting circuit (A line) used in an invasive blood pressure measurement method.

INDUSTRIAL APPLICABILITY

As described above, the flow control apparatus and the injection circuit in the present invention can be applied as constituent components of a transfusion circuit and a drug injection circuit, and have industrial applicability.

The invention claimed is:

1. A medical injection circuit, comprising a flow control apparatus, a first tube, and a second tube,
the flow control apparatus comprising: a tubular outside member having a first and a second opening; a tubular inside member having a first and second opening inserted in the outside member, and a valve member,
wherein the first opening of the inside member and the first opening of the outside member are oriented in the same direction,
the inside member further includes a through-hole passing through a side wall of the inside member in a thickness direction and a contact portion that is in contact with the outside member, which are arranged in that order in a direction from the first opening of the inside member to the second opening thereof,
the valve member is placed in the second opening of the inside member, and passes only a fluid supplied at a set pressure or higher in a direction from the first opening of the inside member to the second opening thereof,
the outside member is formed so as to be deformed elastically, thereby forming a gap communicating with the through-hole between the outside member and the contact portion,
the gap forms a flow path of a fluid in combination with the through-hole,
the first tube is connected to the first opening of the inside member, and
the second tube is connected to the second opening of the outside member.

2. The medical injection circuit according to claim 1, wherein a convex portion is formed along an outer periphery of the inside member, and a top portion of the convex portion forms the contact portion.

3. The medical injection circuit according to claim 1, wherein the inside member further includes a second contact portion that is in contact with the outside member at a portion positioned between the first opening and the through-hole, and
a region of the outside member other than the portion that is in contact with the second contact portion is capable of larger elastic deformation than the portion that is in contact with the second contact portion of the inside member.

4. The medical injection circuit according to claim 3, wherein a groove is formed along an outer periphery of the outside member between the portion that is in contact with the second contact portion of the outside member and the region other than the portion that is in contact with the second contact portion on an outer surface of the outside member.

5. The medical injection circuit according to claim 3, wherein a member protruding from an outer surface of the outside member is provided in the region other than the portion that is in contact with the second contact portion of the outside member.

6. The medical injection circuit according to claim 1, wherein the valve member includes a valve portion in an umbrella shape formed so as to cover and close the second opening of the inside member, and a protruding portion that protrudes from the valve portion and is inserted in the inside member from the second opening of the inside member, and the protruding portion is formed so that a gap to be a flow path of a fluid is present between the protruding portion and an inner surface of the inside member when the protruding portion is inserted in the inside member, is fixed to the inside member while the second opening of the inside member is closed with the valve portion, and further is deformable elastically to release closing by the valve portion when the valve portion is pressed with a fluid supplied through the gap between the inner surface of the inside member and the protruding portion at the set pressure or higher.

7. The medical injection circuit according to claim 3, wherein the outside member includes a thin portion whose thickness is smaller than that in the portion that is in contact with the second contact portion in the region other than the portion that is in contact with the second contact portion.

8. The medical injection circuit according to claim 3, wherein the outside member includes a first portion that is provided on the second opening side of the outside member, the first portion has a diameter smaller than that of the portion of the outside member which is in contact with the first contact portion, a pair of members protruding along the first portion are provided on an end of the second opening side of the outside member, and the pair of members are placed so that one member and the other member are opposed to each other with the first portion interposed therebetween.

* * * * *